United States Patent
Skouta et al.

(10) Patent No.: US 9,988,395 B2
(45) Date of Patent: Jun. 5, 2018

(54) ANTIPARASITIC COMPOSITIONS AND METHODS UTILIZING SUBSTITUTED 5,5,7,7-TETRAMETHYL-4,5,6,7-TETRAHYDROTHIENO[2,3-C]PYRIDINE DERIVATIVES

(71) Applicants: Rachid Skouta, El Paso, TX (US); Rosa A. Maldonado, El Paso, TX (US)

(72) Inventors: Rachid Skouta, El Paso, TX (US); Rosa A. Maldonado, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/622,924

(22) Filed: Jun. 14, 2017

(65) Prior Publication Data

US 2017/0349606 A1    Dec. 7, 2017

Related U.S. Application Data

(62) Division of application No. 15/179,865, filed on Jun. 10, 2016, now abandoned.

(60) Provisional application No. 62/173,845, filed on Jun. 10, 2015.

(51) Int. Cl.
  *C07D 495/04*  (2006.01)
  *C07F 5/02*  (2006.01)
  *C07F 5/04*  (2006.01)

(52) U.S. Cl.
  CPC ............ *C07D 495/04* (2013.01); *C07F 5/025* (2013.01); *C07F 5/04* (2013.01)

(58) Field of Classification Search
  CPC ........... C07D 495/04; C07F 5/025; C07F 5/04
  USPC ........................................................ 514/64
  See application file for complete search history.

(56) References Cited

U.S. PATENT DOCUMENTS 6,951,878 B2    10/2005    Moller et al. .................. 514/360
2011/0077250 A1*    3/2011    Ryder .................... A61K 31/70
                                                  514/236.8

FOREIGN PATENT DOCUMENTS

WO    WO/99/46267    9/1999

OTHER PUBLICATIONS

Berman, *Clinical Infectious Diseases*, 24(4):684-703, 1997.
Berman, *Current Opinion in Infectious Diseases*, 11(6):707-710, 1998.
Sensfuss and Habicher, *Heteroatom Chem.*, 1998, 9, 529-536.

* cited by examiner

Primary Examiner — Yong Chu
(74) Attorney, Agent, or Firm — Norton Rose Fulbright US LLP

(57) ABSTRACT

The present disclosure relates generally to systems, methods, and compounds for therapeutic use against parasitic infections. More particularly, the disclosure relates to anti-parasitic compounds, and methods for making and for using the anti-parasitic compounds, where the anti-parasitic compounds have the general formula:

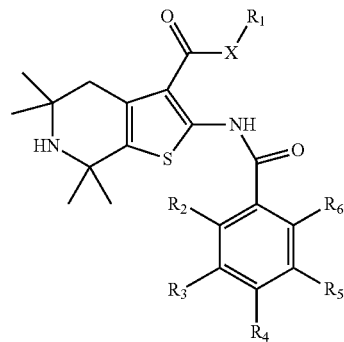

where X, $R_1$, $R_2$, $R_3$, $R_4$, $R_5$, and $R_6$ are defined more fully below.

20 Claims, 16 Drawing Sheets

RS-12

RS-13

GP1-02; MW = 455

GP1-03; MW = 488

GP1-04; MW = 472

GP1-05; MW = 472

GP1-19; MW = 458

GP1-22; MW = 440

RS1-198; MW = 533

RS1-199; MW = 471

RS1-200; MW = 512

RS1-202; MW = 440

ANTIPARASITIC COMPOSITIONS AND METHODS UTILIZING SUBSTITUTED 5,5,7,7-TETRAMETHYL-4,5,6,7-TETRAHYDROTHIENO[2,3-C]PYRIDINE DERIVATIVES

CROSS-REFERENCE TO RELATED APPLICATIONS

This application is a divisional from U.S. Ser. No. 15/179,865 filed Jun. 10, 2016, which claims priority under 35 USC 119 from U.S. 62/173,845 filed Jun. 10, 2015, the contents of each are fully incorporated herein by reference.

STATEMENT REGARDING FEDERALLY SPONSORED RESEARCH

Not Applicable

TECHNICAL FIELD OF THE INVENTION

The present disclosure relates generally to systems, methods, and compounds for therapeutic use against parasitic infections. More particularly, the disclosure relates to antiparasitic compounds, and methods for making and for using the anti-parasitic compounds, where the anti-parasitic compounds are substituted 5,5,7,7-tetramethyl-4,5,6,7-tetrahydrothieno[2,3-C]pyridine derivatives.

BACKGROUND

Parasitic diseases affect millions of people worldwide with severe social and economic consequences. The protozoan parasites *Leishmania major* and *Trypanosoma cruzi* cause leishmaniasis and Chagas' disease (CD), respectively. There are several clinical forms of leishmaniasis: visceral leishmaniasis (VL), muco-cutaneous leishmaniasis (MCL), diffuse cutaneous leishmaniasis (DCL) and cutaneous leishmaniasis (CL). As for CD, 15-30% of the people infected with *T. cruzi* develop manifestations of organ damage, resulting in the cardiac, digestive, or nervous forms of chronic Chagas' disease. Currently, there are between 11-18 million individuals infected with *T. cruzi*, while the overall prevalence of leishmaniasis is 12 million people, with 350 million at risk.

Humans and a wide range of other mammals are usually infected with *T. cruzi* when the triatomine vector defecates while taking a blood meal. The metacyclic trypomastigote form of the parasite contained in the fecal material is inoculated through the bite wound or mucous membranes. The parasite invades host cells where it is transformed into intracellular amastigotes. In this stage they proliferate by binary fission and eventually differentiate into trypomastigotes. The host cell finally ruptures releasing the parasites into the circulation where they can invade other cells or be ingested in a blood meal by an insect vector. *Leishmania* on the other hand, is transmitted by sand flies as metacyclic promastigotes. The proliferative promastigote form then differentiates into the metacyclic form before entering the mammalian host. Once inside the host, the metacyclic form is phagocytosed by macrophages where they differentiate into amastigotes, which proliferate leading to macrophage lysis and further infection of surrounding macrophages.

Despite the advances in understanding the biology of these organisms, most of the drugs still used were developed in colonial times. The current treatment for *T. cruzi* consists of two nitroheterocyclic derivatives, benzinidazol and nifurtimox. These compounds have severe side effects and since the course of treatment lasts from 1-4 months resulting in many incomplete drug schedules, which leads to the development of resistance. In the case of leishmaniasis, pentavalent antimonials are used throughout most endemic regions; however, they are no longer used in India because of drug resistance. In the 1980s, new formulations of amphotericin B encapsulated in liposomes were developed. This drug is highly effective in both VL and CL; however, its high cost limits the wider use of this drug. Despite the ever-increasing need for safe and effective new drugs, their development has been extremely slow.

WO 99/46267 and U.S. Pat. No. 6,951,878 teach that modulators of protein tyrosine phosphatases (PTPases) may play a critical role in parasitic infections. WO 99/46267 US and U.S. Pat. No. 6,951,878 discloses various compounds incorporating a 4,5,6,7-tetrahydro-thieno[2,3-c]pyridyl group and discloses they are useful for modulating PTPase. A publication by authors including one of the present inventors, Rachid Skouta, (Wolpaw et al., "Modulatory profiling identifies mechanisms of small molecule-induced cell death", PNAS, vol. 108, no. 39, pp. 771-780, Sep. 27, 2011) discloses various 4,5,6,7-tetrahydro-thieno[2,3-c]pyridine compounds and discloses that one of them ("NPC25" therein) is useful for inducing mitochondrial cell death. However, the above-listed publications do not provide compounds with demonstrated antiparasitic activity, in particular with demonstrated activity against *Leishmania major* or *Leishmania* species and *T. cruzi*.

Thus there is a need for additional drugs against and treatments for *Leishmania major* or *Leishmania* species and *T. cruzi*.

SUMMARY

In view of the aforementioned problems and trends, embodiments of the present invention provide systems, methods, and compounds for therapeutic use against parasitic infections.

According to a first aspect of the invention, antiparasitic compounds comprise 5,5,7,7-tetramethyl-4,5,6,7-tetrahydrothieno[2,3-C]pyridine derivatives having a general formula of Formula I:

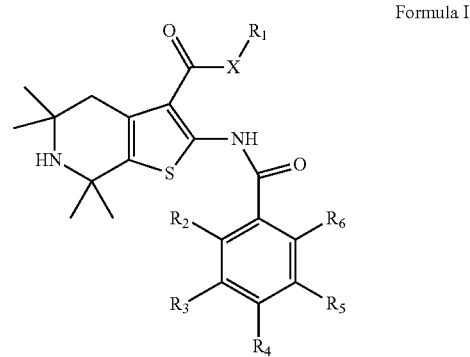

Formula I where X is O or N, $R_1$ is a C2 to C4 alky or cycloalkyl; $R_2$, $R_3$, $R_4$, $R_5$, and $R_6$ are independently selected from hydrogen (H), chlorine (Cl), bromine (Br), fluorine (F), $CF_3$, $SF_5$, substituted or unsubstituted morpholine, substituted or unsubstituted piperazine, boronic acid ($B(OH)_2$), substituted or unsubstituted 1,3,2-dioxaborolane.

In certain aspects X is O; $R_1$ is ethyl, propyl, iso-propyl, cyclopropyl, butyl, isobutyl, sec-butyl or tert-butyl; and $R_2$, $R_3$, $R_4$, $R_5$, and $R_6$ are independently selected from H, F, $CF_3$, $SF_5$, substituted or unsubstituted morpholine, substituted or unsubstituted piperazine, boronic acid ($B(OH)_2$), substituted or unsubstituted 1,3,2-dioxaborlane. In further aspects $R_2$ and $R_6$ are H, and $R_3$, $R_4$, and $R_5$ are F. In still further aspects $R_2$, $R_3$, $R_4$, $R_5$, and $R_6$ are fluorine. In certain aspects $R_3$ or $R_5$ is $CF_3$, $SF_5$, boronic acid, or 4,4,5,5-tetramethyl-1,3,2-dioxaborlane and the other R groups H. In still a further aspect $R_2$, $R_3$, $R_5$, and $R_6$ are H, and $R_4$ is morpholine, methyl-piperazine, $SF_5$, boronic acid, or 4,4,5,5-tetramethyl-1,3,2-dioxaborlane. In certain aspects, $R_2$, $R_3$, $R_4$, $R_5$, and $R_6$ are independently selected from H, Cl, Br, F, and $CF_3$. In still a further aspect, one of $R_2$, $R_3$, $R_4$, $R_5$, and $R_6$ is $CF_3$, another of $R_2$, $R_3$, $R_4$, $R_5$, and $R_6$ is Cl or Br, and the remainder of $R_2$, $R_3$, $R_4$, $R_5$, and $R_6$ are H.

In certain aspects X is N and $R_1$ is ethyl, propyl, isopropyl, cyclopropyl, butyl, isobutyl, sec-butyl or tert-butyl; and $R_2$, $R_3$, $R_4$, $R_5$, and $R_6$ are independently selected from H, F, $CF_3$, $SF_5$, substituted or unsubstituted morpholine, substituted or unsubstituted piperazine, boronic acid ($B(OH)_2$), substituted or unsubstituted 1,3,2-dioxaborlane. In further aspects $R_2$ and $R_6$ are H, and $R_3$, $R_4$, and $R_5$ are F. In still further aspects $R_2$, $R_3$, $R_4$, $R_5$, and $R_6$ are fluorine. In certain aspects $R_3$ or $R_5$ is $CF_3$, $SF_5$, boronic acid, or 4,4,5,5-tetramethyl-1,3,2-dioxaborlane and the other R groups H. In still a further aspect $R_2$, $R_3$, $R_5$, and $R_6$ are H, and $R_4$ is morpholine, methyl-piperazine, $SF_5$, boronic acid, or 4,4,5,5-tetramethyl-1,3,2-dioxaborlane. In certain aspects, $R_2$, $R_3$, $R_4$, $R_5$, and $R_6$ are independently selected from H, Cl, Br, F, and $CF_3$. In still a further aspect, one of $R_2$, $R_3$, $R_4$, $R_5$, and $R_6$ is $CF_3$, another of $R_2$, $R_3$, $R_4$, $R_5$, and $R_6$ is Cl or Br, and the remainder of $R_2$, $R_3$, $R_4$, $R_5$, and $R_6$ are H.

In certain aspects, a method of making a compound having the general formula of Formula I comprises mixing 2,2,6,6-tetramethylpiperidine, a 2-cyanoacetate ester comprising $R_1$, and sulfur in ethanol under heat to form a reaction solution; and adding 2-$R_2$, 3-$R_3$, 4-$R_4$-, 5-$R_5$, 6-$R_6$-benzoyl chloride to the reaction solution at room temperature.

In certain aspects, a method of treating a parasitic infection comprising administering the antiparasitic compound having a general formula of Formula I to a subject in need thereof.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

Other aspects of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

NOTATION AND NOMENCLATURE

Figure 1:
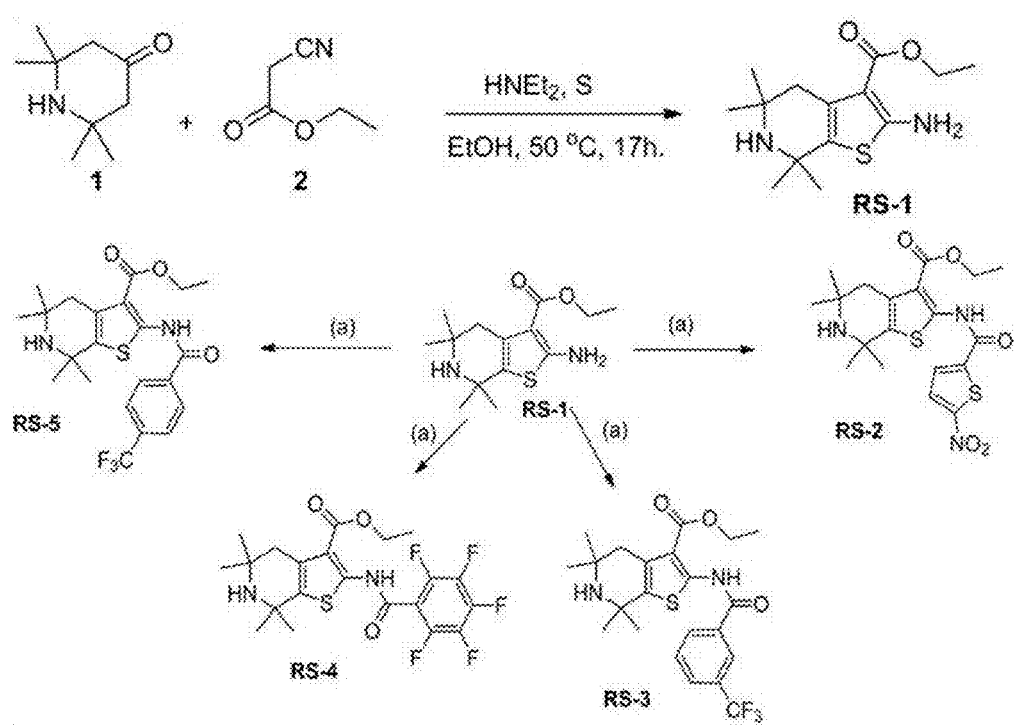
FIG. 1 illustrates a synthesis method, its use to make RS1 to RS5, and their structures.

Certain terms are used throughout the following description and claims to refer to particular system components and configurations. As one skilled in the art will appreciate, the same component may be referred to by different names. This document does not intend to distinguish between components that differ in name but not function. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or.

Various chemical definitions related to compounds described herein are provided as follows.

As used herein, the term "water soluble" means that the compound dissolves in water at least to the extent of 0.010 mole/liter or is classified as soluble according to literature precedence.

As used herein, the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, C1-C4 alkyl, heteroalkyl, alkoxy, alkylthio, alkylamino, (alkyl)$_2$ amino, alkylsulfinyl, alkylsulfonyl, arylsulfonyl, cycloalkyl, heterocyclyl, aryl, and heteroaryl.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C$_{1-4}$ alkylsulfonyl").

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

It is contemplated that any embodiment discussed in this specification can be implemented with respect to any method or composition of the invention, and vice versa. Furthermore, compositions of the invention can be used to achieve methods of the invention.

Trypanosomatids are a group of kinetoplastid protozoa distinguished by having only a single flagellum. All members are exclusively parasitic, found primarily in insects. A few genera have life-cycles involving a secondary host, which may be a vertebrate, invertebrate or plant. These include several species that cause major diseases in humans. The three major human diseases caused by trypanosomatids are—African trypanosomiasis (Sleeping Sickness, caused by *Trypanosoma brucei* and transmitted by Tsetse flies), South American trypanosomiasis (Chagas Disease, caused by *Trypanosoma cruzi* and transmitted by triatomine bugs), and leishmaniasis (a set of trypanosomal diseases caused by various species of *Leishmania* transmitted by sandflies). Certain aspects described herein are directed to compounds and therapies for treating trypanosomatid infections.

Therapies against human leishmaniasis include pentavalent antimonials (sodium stibogluconate and meglumine antimonate) and amphotericin B (Berman, *Clinical Infectious Diseases*, 24(4):684-703, 1997; Berman, *Current Opinion in Infectious Diseases*, 11(6):707-710, 1998). Paromomycin, an aminoglycoside, has also shown anti-*Leishmania* activity, but few patients have been treated and the efficacy has been variable in different areas of the world where it was studied (Berman, *Current Opinion in Infectious Diseases*, 11(6):707-710, 1998). These drugs have several disadvantages: (1) their cost is prohibitively high; (2) they are unavailable for oral administration (some of them like amphotericin B can only be used intravenously); and/or (3) they may cause serious side effects that require close monitoring of the patients (Berman, *Clinical Infectious Diseases*, 24(4):684-703, 1997).

Certain embodiments are directed to 5,5,7,7-tetramethyl-4,5,6,7-tetrahydrothieno[2,3-C]pyridine derivatives having a general formula of Formula I:

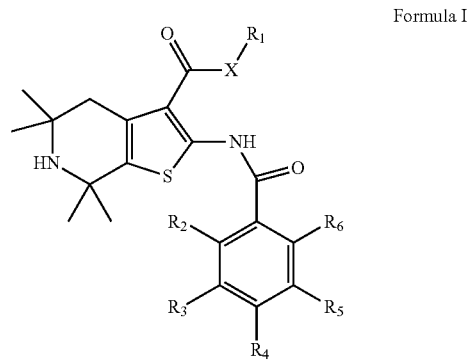

Formula I where X is O or N, $R_1$ is a C2 to C4 alky or cycloalkyl; $R_2$, $R_3$, $R_4$, $R_5$, and $R_6$ are independently selected from hydrogen (H), halogen, alkyl, heteroalkyl, cycloalkyl, heterocyclyl, aryl, heteroaryl, alkoxy, alkylsulfonyl, and boronyl group. In certain aspects $R_2$, $R_3$, $R_4$, $R_5$, and $R_6$ are independently selected from hydrogen, chlorine (Cl), bromine (Br), fluorine (F), $CF_3$, $SF_5$, substituted or unsubstituted morpholine, substituted or unsubstituted piperazine, boronic acid (B(OH)$_2$), substituted or unsubstituted 1,3,2-dioxaborlane.

In certain aspects X is O; $R_1$ is ethyl, propyl, iso-propyl, cyclopropyl, butyl, isobutyl, sec-butyl or tert-butyl; and $R_2$, $R_3$, $R_4$, $R_5$, and $R_6$ are independently selected from H, F, $CF_3$, $SF_5$, substituted or unsubstituted morpholine, substituted or unsubstituted piperazine, boronic acid (B(OH)$_2$), substituted or unsubstituted 1,3,2-dioxaborlane. In further aspects $R_2$ and $R_6$ are H, and $R_3$, $R_4$, and $R_5$ are F. In still further aspects $R_2$, $R_3$, $R_4$, $R_5$, and $R_6$ are fluorine. In certain aspects $R_3$ or $R_5$ is $CF_3$, $SF_5$, boronic acid, or 4,4,5,5-tetramethyl-1,3,2-dioxaborlane and the other R groups H. In still a further aspect $R_2$, $R_3$, $R_5$, and $R_6$ are H, and $R_4$ is morpholine, methyl-piperazine, $SF_5$, boronic acid, or 4,4,5,5-tetramethyl-1,3,2-dioxaborlane. In certain aspects, $R_2$, $R_3$, $R_4$, $R_5$, and $R_6$ are independently selected from H, Cl, Br, F, and $CF_3$. In still a further aspect, one of $R_2$, $R_3$, $R_4$, $R_5$, and $R_6$ is $CF_3$, another of $R_2$, $R_3$, $R_4$, $R_5$, and $R_6$ is Cl or Br, and the remainder of $R_2$, $R_3$, $R_4$, $R_5$, and $R_6$ are H.

In certain aspects X is N and $R_1$ is ethyl, propyl, iso-propyl, cyclopropyl, butyl, isobutyl, sec-butyl or tert-butyl; and $R_2$, $R_3$, $R_4$, $R_5$, and $R_6$ are independently selected from H, F, $CF_3$, $SF_5$, substituted or unsubstituted morpholine, substituted or unsubstituted piperazine, boronic acid (B (OH)$_2$), substituted or unsubstituted 1,3,2-dioxaborlane. In further aspects $R_2$ and $R_6$ are H, and $R_3$, $R_4$, and $R_5$ are F. In still further aspects $R_2$, $R_3$, $R_4$, $R_5$, and $R_6$ are fluorine. In certain aspects $R_3$ or $R_5$ is $CF_3$, $SF_5$, boronic acid, or 4,4,5,5-tetramethyl-1,3,2-dioxaborlane and the other R groups H. In still a further aspect $R_2$, $R_3$, $R_5$, and $R_6$ are H, and $R_4$ is morpholine, methyl-piperazine, $SF_5$, boronic acid, or 4,4,5,5-tetramethyl-1,3,2-dioxaborlane. In certain aspects, $R_2$, $R_3$, $R_4$, $R_5$, and $R_6$ are independently selected from H, Cl, Br, F, and $CF_3$. In still a further aspect, one of $R_2$, $R_3$, $R_4$, $R_5$, and $R_6$ is $CF_3$, another of $R_2$, $R_3$, $R_4$, $R_5$, and $R_6$ is Cl or Br, and the remainder of $R_2$, $R_3$, $R_4$, $R_5$, and $R_6$ are H.

In certain aspects the 5,5,7,7-tetramethyl-4,5,6,7-tetrahydrothieno[2,3-C]pyridine derivative comprises ethyl 5,5,7,7-tetramethyl-2-(3(trifluoromethyl)benzamido)-4,5,6,7-tetrahydrothieno[2,3-c]pyridine-3-carboxylate (herein "RS-3"), ethyl 5,5,7,7-tetramethyl-2-(perfluorobenzamido)-4,5,6,7-tetrahydrothieno[2,3-c]pyridine-3-carboxylate (herein "RS-4") or ethyl 5,5,7,7-tetramethyl-2-(4-(trifluoromethyl)benzamido)-4,5,6,7-tetrahydrothieno[2,3-c]pyridine-3-carboxylate (herein "RS-5"). In certain further aspects the 5,5,7,7-tetramethyl-4,5,6,7-tetrahydrothieno[2,3-C]pyridine derivative comprises ethyl 5,5,7,7-tetramethyl-2-(2-(trifluoromethyl)benzamido)-4,5,6,7-tetrahydrothieno[2,3-c]pyridine-3-carboxylate (herein "GP1-02"), ethyl 2-(5-chloro-2-(trifluoromethyl)benzamido)-5,5,7,7-tetramethyl-4,5,6,7-tetrahydrothieno[2,3-c]pyridine-3-carboxylate (herein "GP1-03"), ethyl 2-(2-fluoro-3-(trifluoromethyl)benzamido)-5,5,7,7-tetramethyl-4,5,6,7-tetrahydrothieno[2,3-c]pyridine-3-carboxylate (herein "GP1-04"), ethyl 2-(4-fluoro-3-(trifluoromethyl)benzamido)-5,5,7,7-tetramethyl-4,5,6,7-tetrahydrothieno[2,3-c]pyridine-3-carboxylate (herein "GP1-05"), methyl 2-(4-fluoro-3-(trifluoromethyl)benzamido)-5,5,7,7-tetramethyl-4,5,6,7-tetrahydrothieno[2,3-c]pyridine-3-carboxylate (herein "GP1-19"), methyl 5,5,7,7-tetramethyl-2-(2-(trifluoromethyl)benzamido)-4,5,6,7-tetrahydrothieno[2,3-c]pyridine-3-carboxylate (herein "GP1-22"), ethyl 2-(4-bromo-3-(trifluoromethyl)benzamido)-5,5,7,7-tetramethyl-4,5,6,7-tetrahydrothieno[2,3-c]pyridine-3-carboxylate (herein "RS-198"), ethyl 5,5,7,7-tetramethyl-2-(4-morpholinobenzamido)-4,5,6,7-tetrahydrothieno[2,3-c]pyridine-3-carboxylate (herein "RS-7", alternately "RS-199"), ethyl 5,5,7,7-tetramethyl-2-(3-(pentafluorosulfanyl)benzamido)-4,5,6,7-tetrahydrothieno[2,3-c]pyridine-3-carboxylate (herein "RS-9", alternately "RS-200"), or ethyl 5,5,7,7-tetramethyl-2-(3,4,5-trifluorobenzamido)-4,5,6,7-tetrahydrothieno[2,3-c]pyridine-3-carboxylate (herein "RS-6", alternately "RS-202").

Certain embodiments are directed to a one-pot synthetic method for compounds described herein. In certain aspects the compounds of Formula I can be synthesized by a method that comprises stirring 2,2,6,6-tetramethylpiperidine with a 2-cyanoacetate ester and sulfur in EtOH at 50° C. The mixture is cooled to room temperature, then an acyl chloride corresponding to the desired compound is added and the reaction is stirred for an additional 1 hour. The solvent is evaporated and the residue is purified by flash-column chromatography on silica gel to provide the desired compound.

In certain aspects the compounds of Formula I can be synthesized by a method that comprises adding diisopropylethylamine (DIPEA) under nitrogen to 3-substituted ethyl 2-amino-5,5,7,7-tetramethyl-4,5,6,7-tetrahydrothieno[2,3-c]pyridine in dry dichloromethane (DCM) followed by adding at 0° C. an acyl chloride. Aqueous bicarbonate is added and the organic phases are separated. The aqueous phase is extracted with dichloromethane (DCM) or similar solvent. After drying with anhydrous magnesium sulfate the solvent is removed under vacuum. The crude product is purified by silica gel.

In certain further embodiments the acyl chlorides include, but are not limited to, 5-nitrothiophene-2-carbonyl chloride, 3-(trifluoromethyl)benzoyl chloride, 2,3,4,5,6-pentafluorobenzoyl chloride or 4-(trifluoromethyl)benzoyl chloride. In certain yet further embodiments, the acyl chlorides include, but are not limited to, 2-(trifluoromethyl)benzoyl chloride, trifluoromethyl)benzoyl chloride, 2-fluoro-3-(trifluoromethyl)benzoyl chloride, 4-fluoro-3-(trifluoromethyl)benzoyl chloride, 4-fluoro-3-(trifluoromethyl)benzoyl chloride, 2-(trifluoromethyl)benzoyl chloride, 4-bromo-3-(trifluoromethyl)benzoyl chloride, 4-morpholinobenzoyl chloride, 3-(pentafluorosulfanyl)benzoyl chloride or 3,4,5-trifluorobenzoyl chloride.

Certain embodiments are directed to methods of treating eukaryotic parasites comprising administering an effective amount of an 5,5,7,7-tetramethyl-4,5,6,7-tetrahydrothieno[2,3-C] pyridine derivative having a general formula of Formula I. In certain aspects the 5,5,7,7-tetramethyl-4,5,6,7-tetrahydrothieno[2,3-C] pyridine derivative having a general formula of Formula I is administered at a dose of between 50, 100, 150, 200, 250, 300, 400 500 to 250, 300, 350, 400, 450, 500, 550, 600, 700, 800, 900 mg/day, including all values and ranges there between. In certain aspects 50, 100, 150, 200, 250, 300, 350, 400, 450, 500, 550, 600, 700, 800, 900, 1000 mg of 5,5,7,7-tetramethyl-4,5,6,7-tetrahydrothieno[2,3-C] pyridine derivative having a general formula of Formula I is administered. In a further aspect the 5,5,7,7-tetramethyl-4,5,6,7-tetrahydrothieno[2,3-C] pyridine derivative having a general formula of Formula I is administered in one dose or in multiple doses over 0.5, 1, 2, 3, 4, 5, 6, 7, 8, 9, or 10 minutes, hours or days. The 5,5,7,7-tetramethyl-4,5,6,7-tetrahydrothieno[2,3-C] pyridine derivative having a general formula of Formula I can be formulated as a tablet, a capsule, or a solution. In certain aspects the 5,5,7,7-tetramethyl-4,5,6,7-tetrahydrothieno[2,3-C] pyridine derivative having a general formula of Formula I is administered orally or intravascularly. In certain aspects the 5,5,7,7-tetramethyl-4,5,6,7-tetrahydrothieno[2,3-C] pyridine derivative having a general formula of Formula I can be administered in combination with other anti-parasite therapies. In certain embodiments the parasite is *Leishmania major* or *Trypanosoma cruzi*.

In certain embodiments the compounds of Formula I can be formulated for administration to a subject (i) having a parasite infection, (ii) located in a geographic region endemic to a parasite, or (iii) at risk of parasite infection, e.g., are present in a local area in the midst of an outbreak. Acceptable formulation components for pharmaceutical preparations are nontoxic to recipients at the dosages and concentrations employed. In addition to the anti-parasitic agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophobic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see Remington's Pharmaceutical Sciences, 18th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to intravenous, intraperitoneal, oral, or intraarterial. In certain aspects an anti-parasitic agent will be administered orally. When administering the compositions by injection, the administration may be by continuous infusion or by single or multiple boluses. For parenteral administration, the anti-parasitic agents may be administered in a pyrogen-free, parenterally acceptable solution comprising the desired anti-parasitic agents in a pharmaceutically acceptable vehicle. A particularly suitable vehicle for parenteral injection is one in which one or more anti-parasitic agents are formulated as a sterile solution and properly preserved.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, a compound of Formula I may be mixed with a binder, a lubricant, absorption enhancer, an inert diluent and/or a disintegrating agent. The compound of Formula I may be mixed with a binder, such as microcrystalline cellulose, and a surfactant, such as sodium lauryl sulphate until a homogeneous mixture obtained. Subsequently, another binder, such as polyvinylpyrrolidone (polyvidone), may be transferred to the mixture under stirring with a small amount of added water. This mixture may be passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical. Parenteral administration also includes a stable emulsion of the designed for intravenous use.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides or nerolidol, a sesquiterpene.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as DMSO, oil, sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts. In certain aspects the composition are 10 to 30% DMSO and/or oil (e.g., sesame oil).

The components used to formulate the pharmaceutical compositions are preferably of high purity and are substantially free of potentially harmful contaminants (e.g., at least National Food (NF) grade, generally at least analytical grade, and more typically at least pharmaceutical grade). Compositions for parental administration are also sterile, substantially isotonic and made under GMP conditions.

For the compounds of the present invention, alone or as part of a pharmaceutical composition, such doses are between about 0.001 mg/kg and 1 mg/kg body weight, preferably between about 1 and 100 μg/kg body weight, most preferably between 1 and 10 μg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

Patients which can be treated include mammals such as a dog, cat, horse, cow, cattle, pig, sheep, goat, rodents, camels or chicken, or a wild animal, but is preferably a human. Administration may be to an adult, an adolescent, a child, a neonate or an infant, or even to a patient in utero.

Positive effects of treatment include a reduction of parasite load or parasitemia, death or inactivation of the parasite, decreased activity of the parasite, or elimination of the parasite from the body. Preferably, the parasite load is reduced at least 50%, more preferably 80%, and even more preferably is undetectable after treatment. Alternately or combination, the parasite activity is reduced at least 50%, more preferably 80%, and even more preferably is undetectable after treatment. It will be understood that measurements and assays of parasite survival, cytotoxicity, and proliferation are capable to exemplify the positive effects of treatment.

A number of references have been cited, the disclosures of which are incorporated herein by reference to the extent that they do not conflict with the present disclosure.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Table 1 provides a summary of various results described and illustrated further in the examples. In particular, table 1 illustrates positive effects of treatment with the present compounds. More particular, Table 1 illustrates antiparasitic activity, cytotoxicity to macrophages, and proliferation evaluation of selected compounds. $IC_{50}$ is median inhibitory concentration. TI is therapeutic index. Table 1 shows in tabular form the results plotted in FIGS. 2-4 and FIGS. 14-16. More particularly, the second column shows results corresponding to Example 7 (FIG. 3) and Example 22 (FIG. 16) with respect to cytotoxicity evaluation, for which intraperitoneal macrophages (IPΦ) were treated with RS2, RS3, RS4, GP1-04, and GP1-05 for 48 hrs. Further, the third column shows results corresponding to Example 6 (FIG. 2) and Example 21 (FIG. 14 and FIG. 15), in particular antiparasitic activity of compounds RS1 to RS5 and GP1-02 to GP105 in *L. major* Luciferase promastigotes for 72 hr. Still further, the fourth column shows results corresponding to Example 8 (FIG. 5), in particular an evaluation of compounds RS1 to RS5 in the proliferation of *T. cruzi* trypomastigotes inside Human Osteoblasts after 48 H treatment.

TABLE 1

| Compound | Mammalian cells $LD_{50}$ (µM) Raw 264.7 Macrophages | *L. major* $LD_{50}$ (µM) Promastigotes $LD_{50}$ (µM) [TI] | *T. cruzi* $LD_{50}$ (µM) Epimastigotes/ Trypomastigotes $IC_{50}$ (µM) [TI] |
|---|---|---|---|
| RS1 | | 10.44 | Trypomastigotes <10 |
| RS2 | ~32 | >10 [3.2] | Epimastigotes ~7.5 [4.26] Trypomastigotes <1.25 |
| RS3 | >40 | 9.51 [4.20] | Trypomastigotes ~<1.25 |
| RS4 | ~15 | 0.671 [22.35] | Trypomastigotes ~<0.156 |
| RS5 | | 10.65 | Trypomastigotes 7.5 |
| GP1-02 | | 6.021 | |
| GP1-03 | | 4.878 | |
| GP1-04 | 17 | 0.169 [100.59] | |
| GP1-05 | 22 | 0.780 [28.20] | |
| GP1-19 | | 3.125 | |
| GP1-22 | | 5.640 | |

Example 1: Synthesis of Compounds RS2 to RS5

Referring to FIG. 1, Example 1 illustrates synthesis of ethyl 5,5,7,7-tetramethyl-2-(5-nitrothiophene-2-carboxamido)-4,5,6,7-tetrahydrothieno[2,3-c]pyridine-3-carboxylate ("RS2" or "RS-2"), Ethyl 5,5,7,7-tetramethyl-2-(3-(trifluoromethyl)benzamido)-4,5,6,7-tetrahydro-thieno[2,3-c]pyridine-3-carboxylate ("RS3" or "RS-3"), Ethyl 5,5,7,7-tetramethyl-2-(perfluorobenzamido)-4,5,6,7-tetrahydrothieno[2,3c]pyridine-3-carboxylate ("RS4" or "RS-4"), and Ethyl 5,5,7,7-tetramethyl-2-(4-(trifluoromethyl)benzamido)-4,5,6,7-tetrahydrothieno[2,3-c]pyridine-3-carboxylate ("RS5" or "RS-5").

Referring to FIG. 1, Ethyl 2-amino-5,5,7,7-tetramethyl-4,5,6,7-tetrahydrothieno[2,3-C]pyridine-3-carboxylate ("RS1" or "RS-1") was prepared as shown in the top scheme (Sensfuss and Habicher, *Heteroatom Chem.*, 1998, 9, 529-536). Synthesis "(a)" proceeded as follows. Diisopropylethylamine (DIPEA) was added to RS-1 in dichloromethane (DCM). Various acyl chlorides were added. Aqueous bicarbonate was added and the organic phases were separated. The aqueous phases were extracted Dichloromethane (DCM). After drying with anhydrous magnesium sulfate the solvents were removed. The crudes were purified by silica gel.

Example 2: Ethyl 5,5,7,7-tetramethyl-2-(5-nitrothiophene-2-carboxamido)-4,5,6,7-tetrahydrothieno[2,3-c]pyridine-3-carboxylate (RS-2)

Diisopropylethylamine (DIPEA) (67 µL, 0.389 mmol) was added under nitrogen to ethyl 2-amino-5,5,7,7-tetramethyl-4,5,6,7-tetrahydrothieno[2,3-c]pyridine-3-carboxylate (RS-1) (100 mg, 0.354 mmol) in dry dichloromethane (DCM). At 0° C. 5-nitrothiophene-2-carbonyl chloride (73.9 mg, 0.389 mmol) was added and the mixture was stirred for 17 h at room temperature. Aqueous bicarbonate was added and the organic phases were separated. The aqueous phases were extracted three times with Dichloromethane (DCM). After drying with anhydrous magnesium sulfate the solvents were removed under vacuum. The crudes were purified by silica gel to provide the solid RS-2 (120 mg, 0.274 mmol, 78%). $^1$H NMR (CDCl$_3$, 400 MHz, ppm) δ 12.44 (b, NH), 8.01 (d, J=8.0 Hz, 1H), 7.66 (d, J=8.0 Hz, 1H), 4.39 (q, J=6.8 Hz, 2H), 2.70 (s, 2H), 1.52 (s, 6H), 1.41 (t, J=6.8 Hz, 3H), 1.24 (s, 6H); MS (APCI+, M+1) 438.19.

Example 3: Ethyl 5,5,7,7-tetramethyl-2-(3-(trifluoromethyl)benzamido)-4,5,6,7-tetrahydro-thieno[2,3-c]pyridine-3-carboxylate (RS-3)

Diisopropylethylamine (DIPEA) (67 µL, 0.389 mmol) was added under nitrogen to ethyl 2-amino-5,5,7,7-tetramethyl-4,5,6,7-tetrahydrothieno[2,3-c]pyridine-3-carboxylate (RS-1) (100 mg, 0.354 mmol) in dry dichloromethane (DCM). At 0° C. 3-(trifluoromethyl)benzoyl chloride (57.6 µL, 0.389 mmol) was added and the mixture was stirred for 17 h at room temperature. Aqueous bicarbonate was added and the organic phases were separated. The aqueous phases were extracted three times with Dichloromethane (DCM). After drying with anhydrous magnesium sulfate the solvents were removed under vacuum. The crudes were purified by silica gel to provide the solid RS-3 (95 mg, 0.209 mmol, 60%). $^1$H NMR (CDCl$_3$, 400 MHz, ppm) δ 12.44 (b, NH), 8.30 (s, 1H), 8.15 (d, J=8.0 Hz, 1H), 7.86 (d, J=8.0 Hz, 1H), 7.68 (t, J=8.0 Hz, 1H), 4.41 (q, J=6.8 Hz, 2H), 2.74 (s, 2H), 1.55 (s, 6H), 1.43 (t, J=6.8 Hz, 3H), 1.25 (s, 6H); MS (APCI+, M+1) 455.66.

Example 4: Ethyl 5,5,7,7-tetramethyl-2-(perfluorobenzamido)-4,5,6,7-tetrahydrothieno[2,3-c]pyridine-3-carboxylate (RS-4)

Diisopropylethylamine (DIPEA) (67 µL, 0.389 mmol) was added under nitrogen to ethyl 2-amino-5,5,7,7-tetramethyl-4,5,6,7-tetrahydrothieno[2,3-c]pyridine-3-carboxylate (RS-1) (100 mg, 0.354 mmol) in dry dichloromethane (DCM). At 0° C. 2,3,4,5,6-pentafluorobenzoyl chloride (53.9 µL, 0.389 mmol) was added and the mixture was stirred for 17 h at room temperature. Aqueous bicarbonate was added and the organic phases were separated. The aqueous phases were extracted three times with Dichloromethane (DCM). After drying with anhydrous magnesium sulfate the solvents were removed under vacuum. The crudes were purified by silica gel to provide the solid RS-4 (75 mg, 0.157 mmol, 45%). $^1$H NMR (CDCl$_3$, 400 MHz, ppm) δ 12.10 (b, NH), 4.37 (q, J=7.2 Hz, 2H), 3.05 (s, 2H), 1.89 (s, 6H), 1.60 (s, 6H), 1.38 (t, J=7.2 Hz, 3H); MS (APCI+, M+1) 477.07.

Example 5: Ethyl 5,5,7,7-tetramethyl-2-(4-(trifluoromethyl)benzamido)-4,5,6,7-tetrahydrothieno[2,3-c]pyridine-3-carboxylate (RS-5)

Diisopropylethylamine (DIPEA) (67 µL, 0.389 mmol) was added under nitrogen to ethyl 2-amino-5,5,7,7-tetramethyl-4,5,6,7-tetrahydrothieno[2,3-c]pyridine-3-carboxylate (RS-1) (100 mg, 0.354 mmol) in dry dichloromethane (DCM). At 0° C. 4-(trifluoromethyl)benzoyl chloride (57.9 µL, 0.389 mmol) was added and the mixture was stirred for 17 h at room temperature. Aqueous bicarbonate was added and the organic phases were separated. The aqueous phases were extracted three times with Dichloromethane (DCM). After drying with anhydrous magnesium sulfate the solvents were removed under vacuum. The crudes were purified by silica gel to provide the solid RS-5 (107 mg, 0.235 mmol, 66%). $^1$H NMR (CDCl$_3$, 400 MHz, ppm) δ 12.49 (b, NH), 8.13 (d, J=8.0 Hz, 1H), 7.80 (d, J=8.0 Hz, 1H), 8.15 (d, J=8.0 Hz, 1H), 7.86 (d, J=8.0 Hz, 2H), 7.68 (t, J=8.0 Hz, 2H), 4.41 (q, J=7.2 Hz, 2H), 2.74 (s, 2H), 1.55 (s, 6H), 1.43 (t, J=7.2 Hz, 3H), 1.25 (s, 6H); MS (APCI+, M+1) 455.00.

Example 6: Antiparasitic Activity

Figure 2:
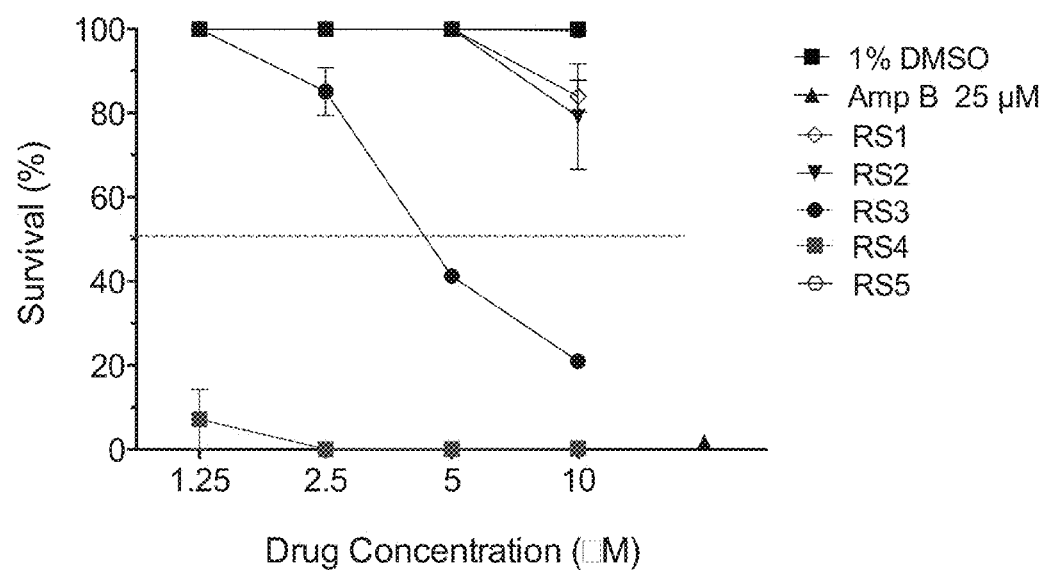
FIG. 2 illustrates antiparasitic activity of compounds RS1 to RS5.

This example illustrates positive effects of treatment with the present compounds. FIG. 2 shows antiparasitic activity of compounds RS1 to RS5 in *L. major* Luciferase promastigotes for 72 hr.

Example 7: Cytotoxicity Evaluation

Figure 3:
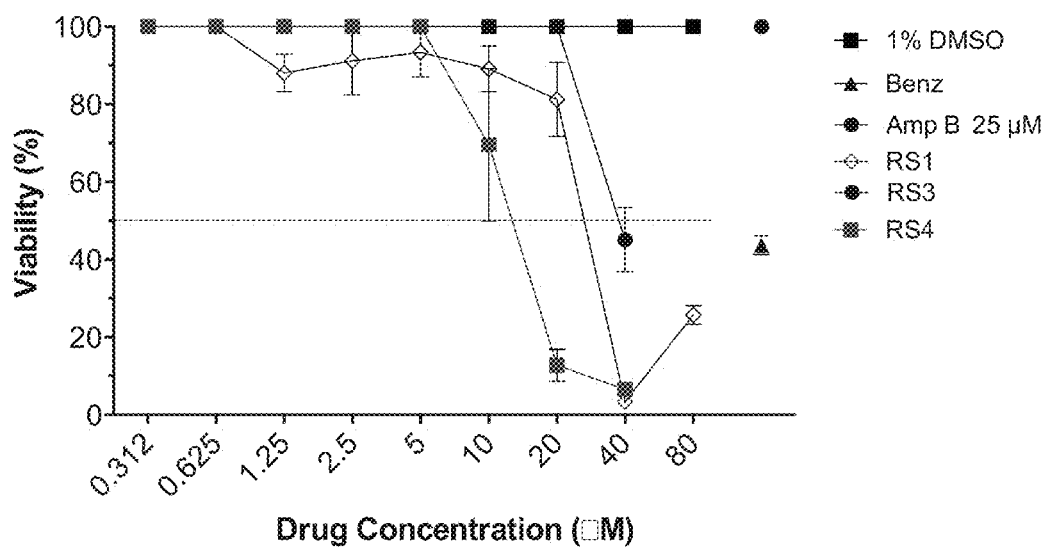
FIG. 3 illustrates a cytotoxicity evaluation of compounds RS1, RS3, and RS4.

This example further illustrates positive effects of treatment with the present compounds. FIG. 3 shows a cytotoxicity evaluation of compounds R1, R3 and R4 Raw 264.7 Macrophages treated with RS1 for 96 hrs. The intraperitoneal macrophages (IPΦ) were treated with RS3, RS4 and RS6 for 48 hrs.

Example 8: Proliferation Assay

Figure 4:
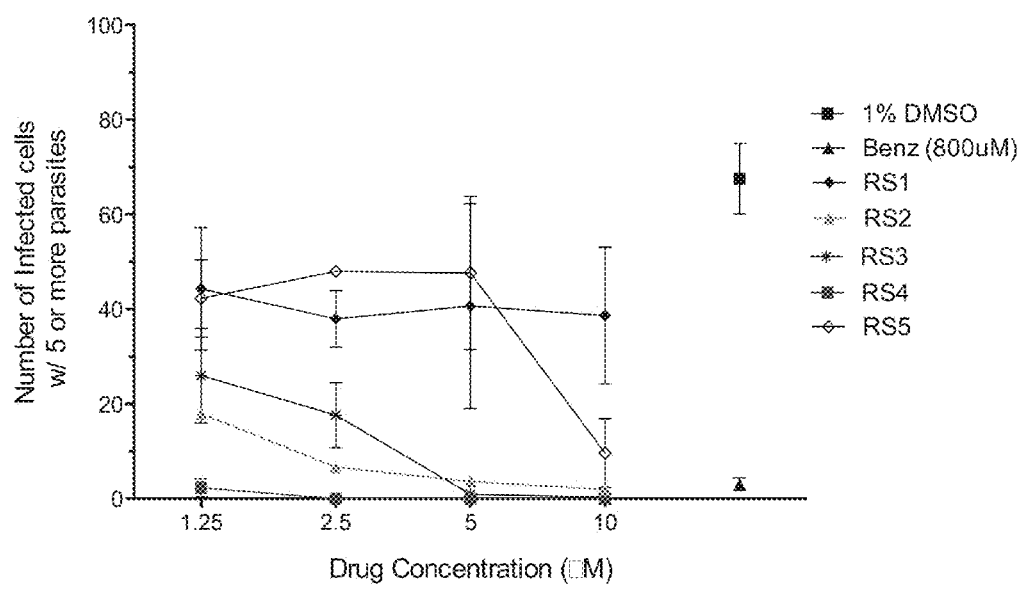
FIG. 4 illustrates a proliferation assay evaluation of compounds RS1 to RS5.
Figure 5:
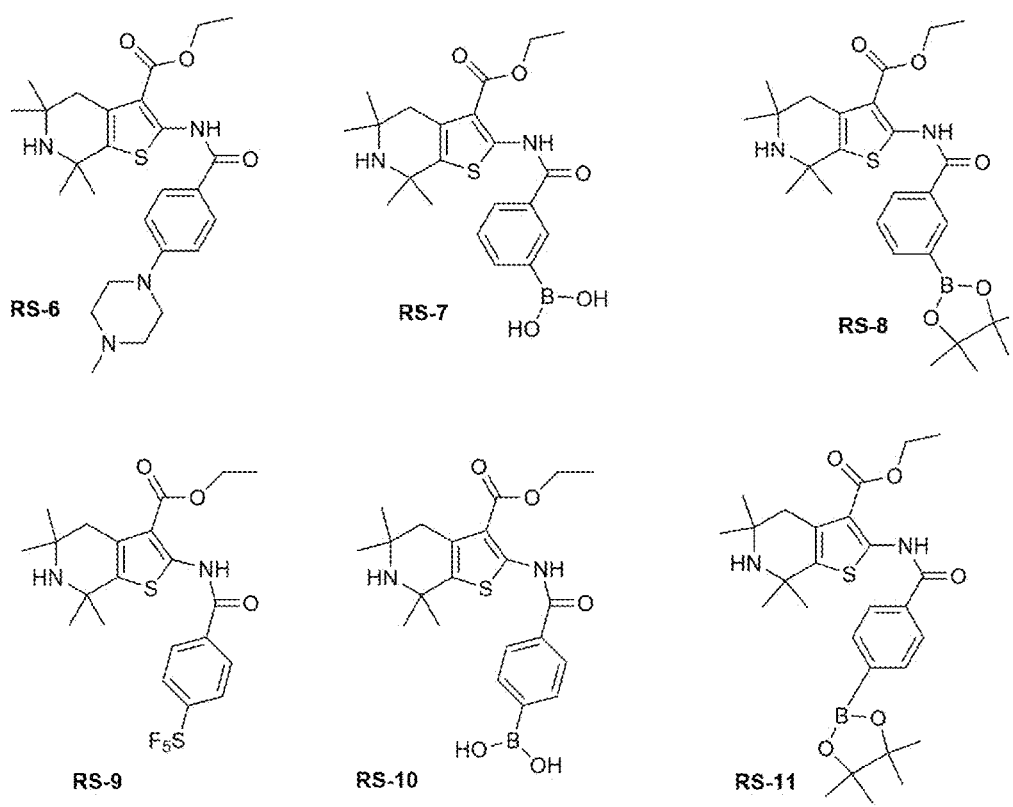
FIGS. 5-8 illustrate various examples of derivative compounds described.
Figure 6:
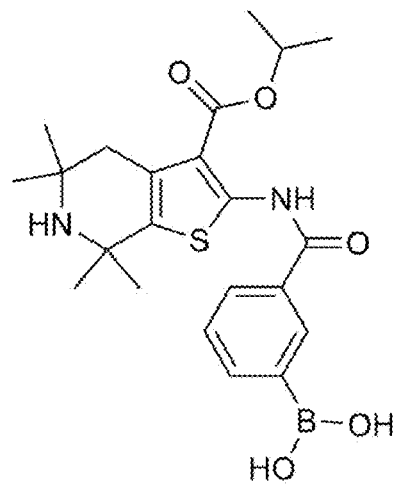
Figure 6:
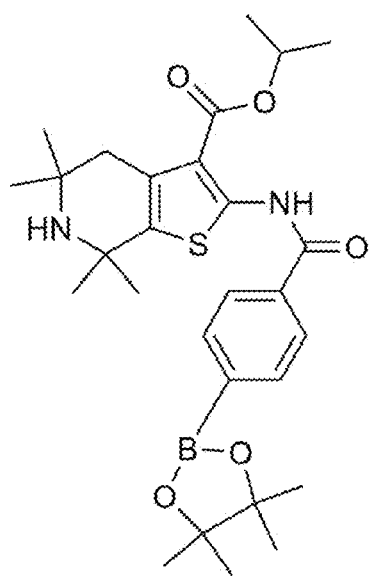
Figure 7:
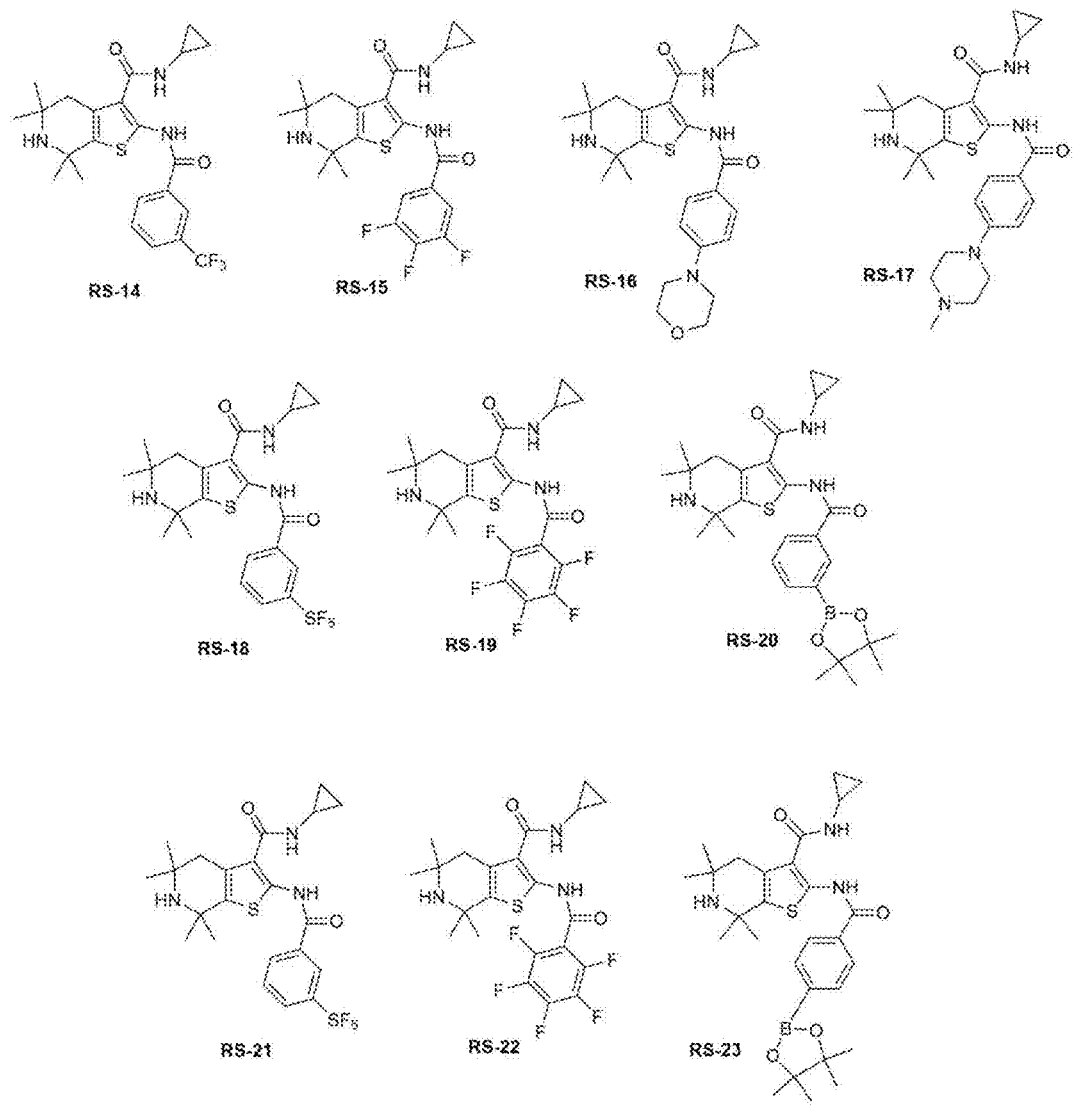
Figure 8:
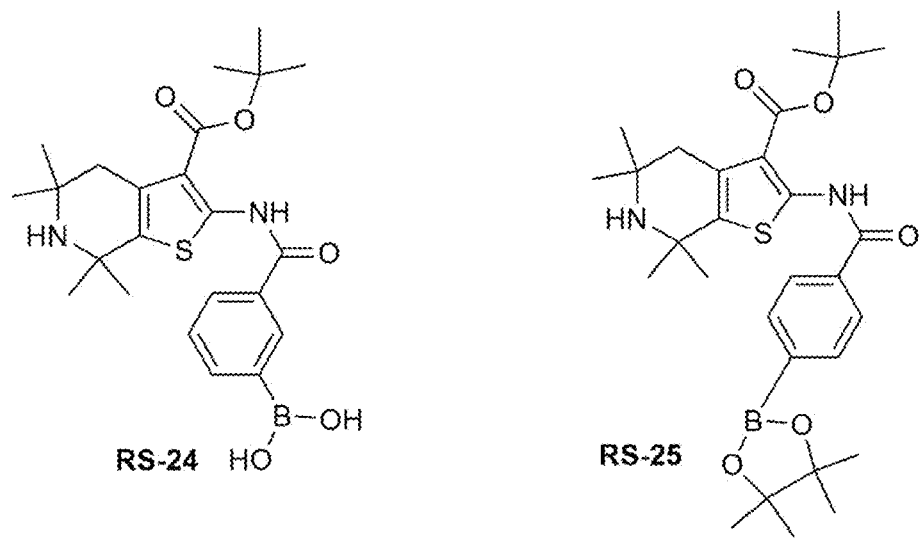

This example further illustrates positives effects of treatment with the present compounds. FIG. 4 shows a proliferation assay, an evaluation of compounds RS1 to RS5 in the proliferation of *T. cruzi* trypomastigotes inside Human Osteoblasts after 48 H treatment. The negative control was treated with 1% DMSO. The positive control was treated with Amp B at 800 µM.

Example 9: Various Additional Exemplary Compounds

FIGS. 5-8 and FIGS. 10-13 illustrate various examples of derivative compounds described.

Example 10: Synthesis of the Compounds of FIG. 6

Figure 9:
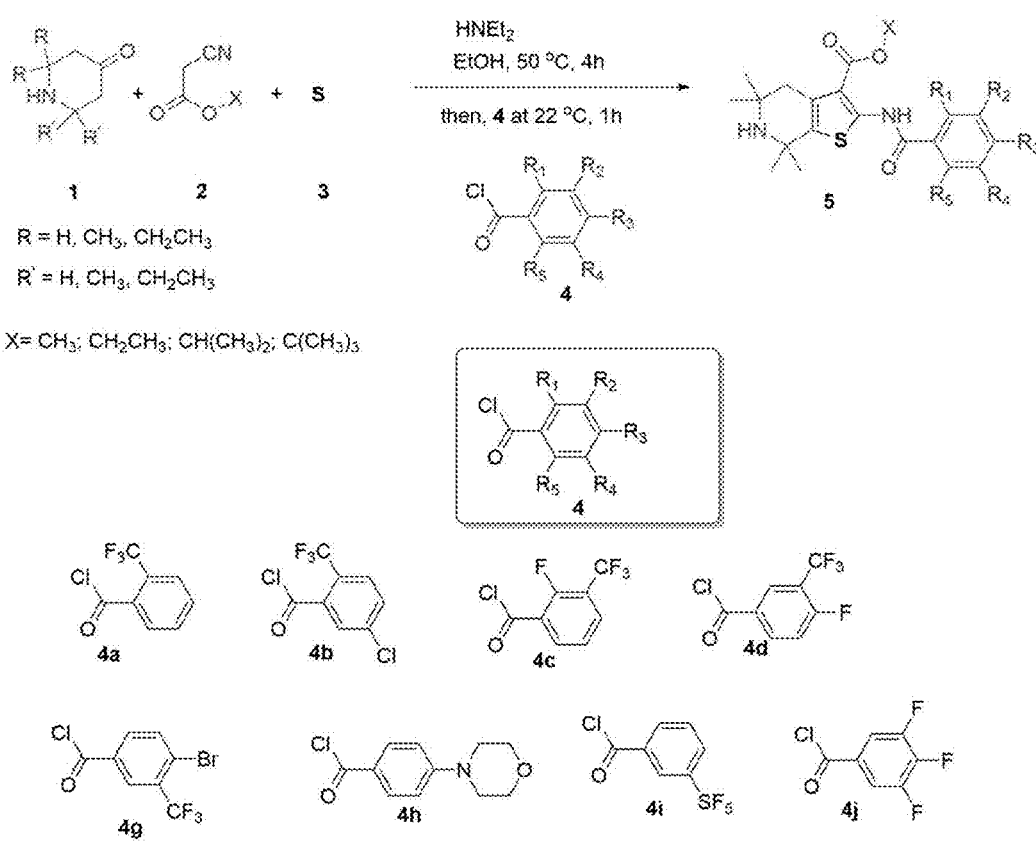
FIG. 9 illustrates another synthesis method and its use to make the compounds illustrated in FIG. 10.
Figure 10:
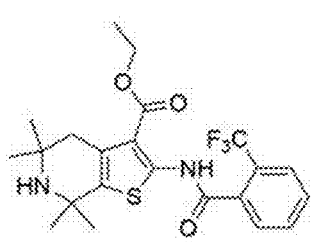
FIGS. 10-13 illustrate various additional examples of derivative compounds described.
Figure 10:
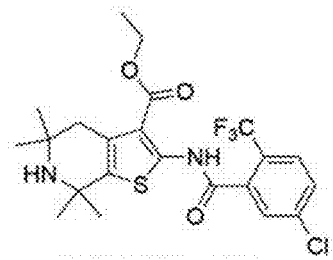
Figure 10:
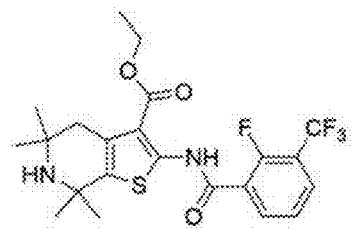
Figure 10:
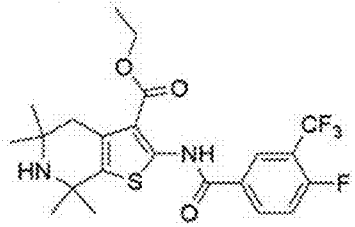
Figure 10:
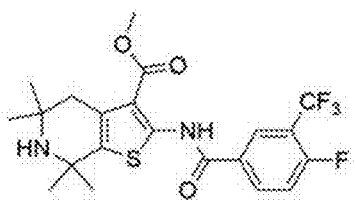
Figure 10:
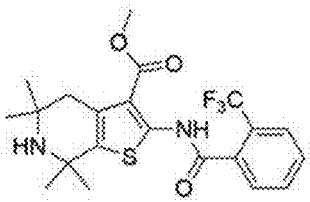
Figure 10:
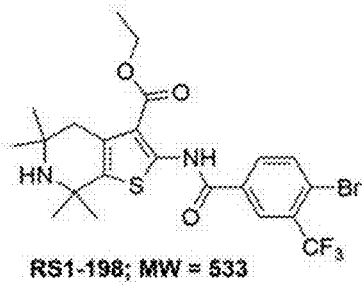
Figure 10:
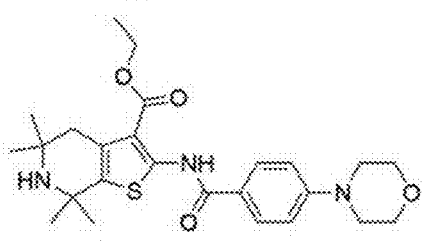
Figure 10:
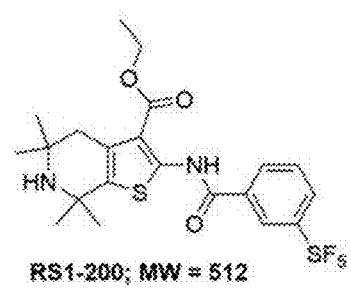
Figure 10:
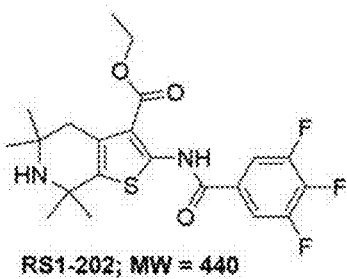
Figure 11:
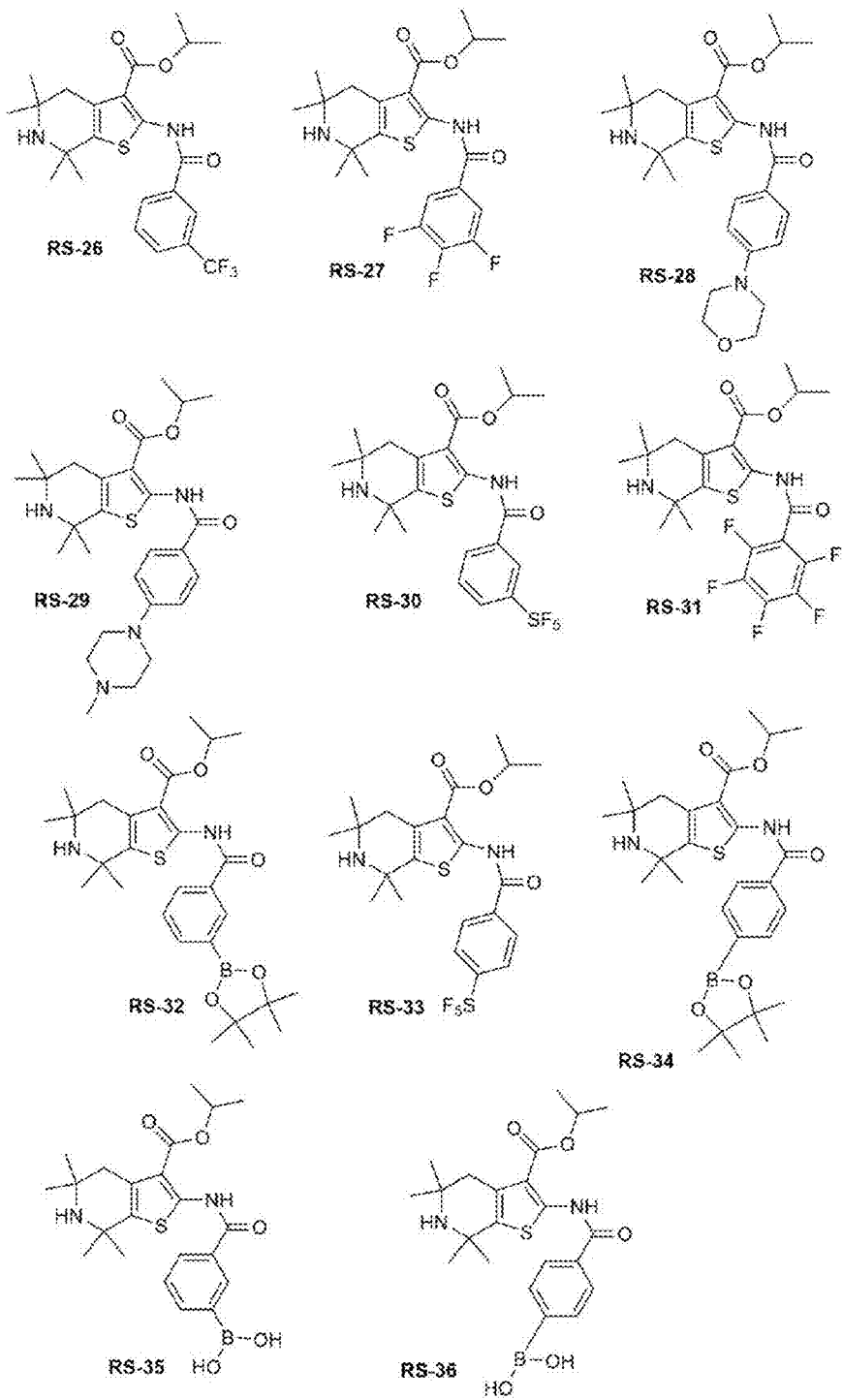
Figure 12:
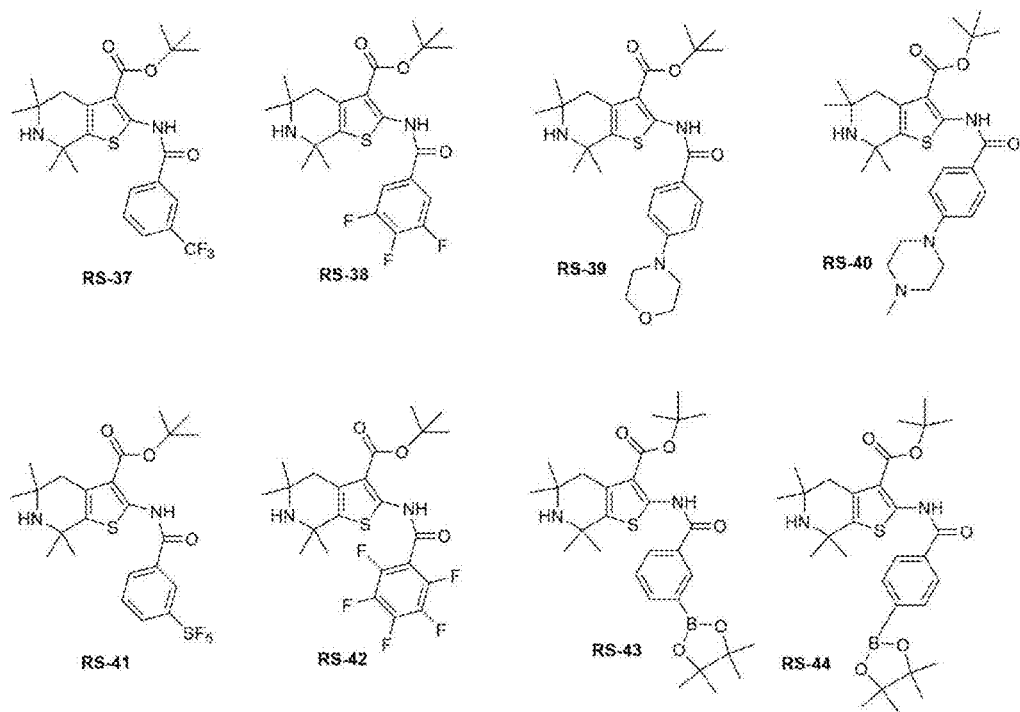
Figure 13:
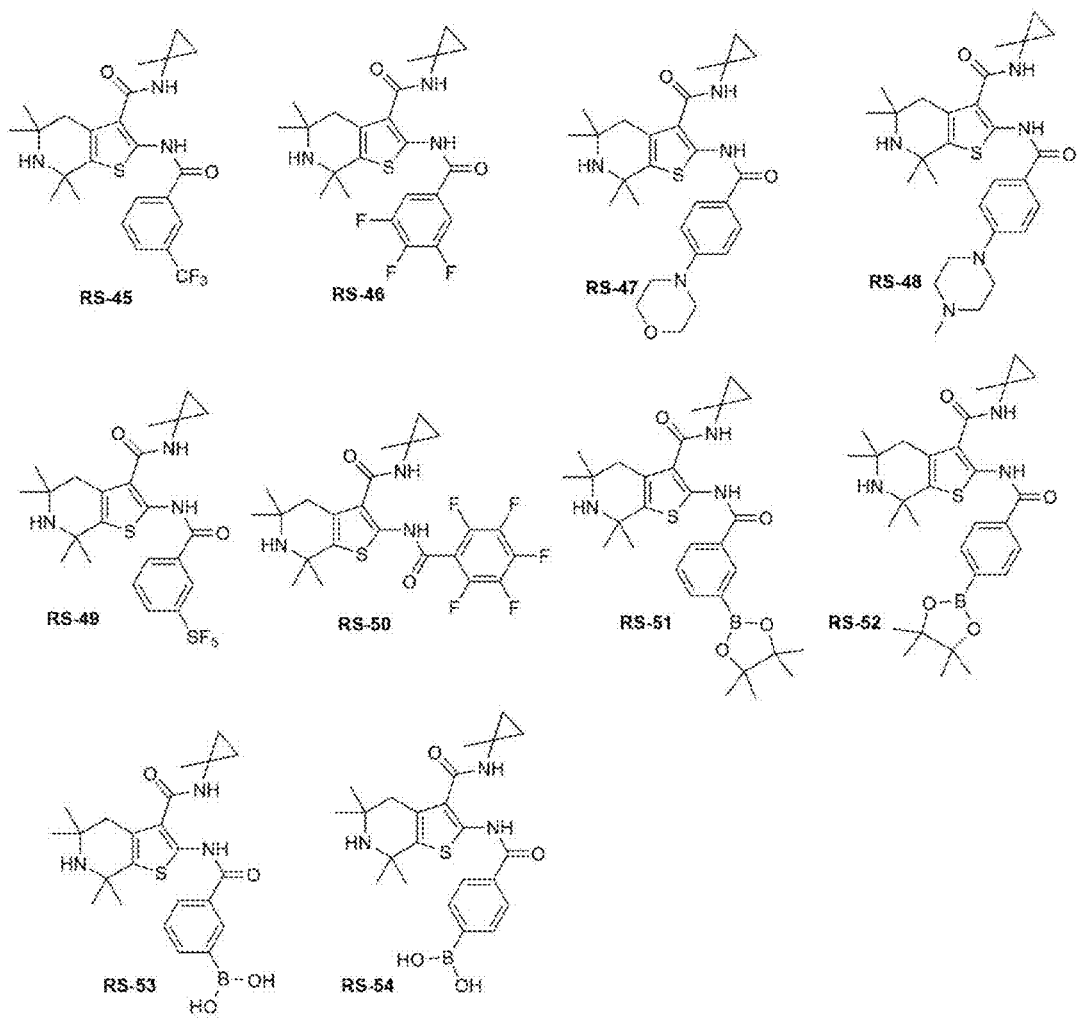

FIG. 9 illustrates a synthesis of the compounds of FIG. 10. 2,2,6,6-tetramethylpiperidine was stirred with a 2-cyanoacetate ester and sulfur in EtOH at 50° C. The mixture was cooled to room temperature, then a benzoyl chloride corresponding to one of the desired compounds was added and the reaction is stirred for an additional 1 hour. The solvent was evaporated and the residue was purified by flash-column chromatography on silica gel to provide the desired compound.

Example 11: Ethyl 5,5,7,7-tetramethyl-2-(2-(trifluoromethyl)benzamido)-4,5,6,7-tetrahydrothieno[2,3-c]pyridine-3-carboxylate (GP1-02)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then 2-(trifluoromethyl)benzoyl chloride (1 equivalent) was added and the reaction was stirred for an additional 1 hour. The solvent was evaporated and the residue was purified by flash-column chromatography on silica gel to provide the desired compound. $^1$H NMR (400 MHz, CDCl$_3$) δ 11.68 (s, 3H), 7.70 (dd, J=29.3, 22.5 Hz, 13H), 4.32 (dd, J=10.6, 7.0 Hz, 7H), 4.01 (dd, J=11.0, 5.4 Hz, 11H), 2.70 (d, J=10.5 Hz, 8H), 1.53 (d, J=10.4 Hz, 20H), 1.39-1.32 (m, 13H), 1.25-1.16 (m, 80H). $^{13}$C NMR (101 MHz, CDCl$_3$) δ 166.18, 163.70, 147.33, 135.09, 133.90, 132.18, 130.71, 128.50, 128.32, 126.68, 112.30, 77.68, 77.36, 77.04, 60.61, 53.42, 51.89, 49.84, 39.53, 34.13, 29.99, 14.00. LC/MS (ESI+): 456.56.

Example 12: Ethyl 2-(5-chloro-2-(trifluoromethyl)benzamido)-5,5,7,7-tetramethyl-4,5,6,7-tetrahydrothieno[2,3-c]pyridine-3-carboxylate (GP1-03)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature then trifluoromethyl)benzoyl chloride (1 equivalent) was added and the reaction was stirred for an additional 1 hour. The solvent was evaporated and the residue was purified by flash-column chromatography on silica gel to provide the desired compound. $^1$H NMR (400 MHz, CDCl$_3$) δ 11.56 (s, 1H), 7.52 (d, J=7.6 Hz, 1H), 7.47 (s, 1H), 7.40 (d, J=6.8 Hz, 1H), 4.10 (d, J=6.1 Hz, 2H), 2.53 (s, 2H), 1.91 (s, 1H), 1.32 (s, 6H), 1.14 (s, 3H), 1.03 (s, 6H). $^{13}$C NMR (101 MHz, CDCl$_3$) δ 166.05, 162.14, 146.93, 138.40, 135.50, 135.04, 130.73, 128.58, 128.43, 128.25, 128.21, 126.63, 126.30, 125.97, 125.65, 124.25, 121.53, 112.53, 60.69, 53.42, 52.17, 50.17, 39.27, 33.88, 31.43, 29.71, 13.96. LC/MS (ESI+): 489.02.

Example 13: Ethyl 2-(2-fluoro-3-(trifluoromethyl)benzamido)-5,5,7,7-tetramethyl-4,5,6,7-tetrahydrothieno[2,3-c]pyridine-3-carboxylate (GP1-04)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then 2-fluoro-3-(trifluoromethyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.40 (d, J=10.3 Hz, 1H), 8.49-8.30 (m, 1H), 7.83 (dd, J=10.5, 3.9 Hz, 1H), 7.45 (t, J=7.8 Hz, 1H), 4.42 (q, J=7.1 Hz, 2H), 2.74 (s, 2H), 1.54 (s, 6H), 1.42 (t, J=7.1 Hz, 3H), 1.23 (t, J=7.1 Hz, 7H). ¹³C NMR (101 MHz, CDCl₃) δ 165.69, 158.56, 158.53, 146.73, 136.26, 135.52, 131.26, 129.09, 124.93, 124.89, 123.49, 121.55, 121.44, 113.11, 60.90, 53.44, 52.28, 50.29, 39.60, 34.23, 30.10, 14.30. LC/MS (ESI+): 473.05.

Example 14: Ethyl 2-(4-fluoro-3-(trifluoromethyl) benzamido)-5,5,7,7-tetramethyl-4,5,6,7-tetrahydrothieno[2,3-c]pyridine-3-carboxylate (GP1-05)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then 4-fluoro-3-(trifluoromethyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.40 (s, 1H), 8.25 (dd, J=6.4, 1.4 Hz, 1H), 8.10 (ddd, J=7.9, 4.1, 2.2 Hz, 1H), 7.29 (t, J=9.1 Hz, 1H), 5.23 (s, 1H), 4.34 (q, J=7.1 Hz, 2H), 2.65 (s, 2H), 1.46 (s, 6H), 1.36 (t, J=7.1 Hz, 3H), 1.16 (d, J=11.3 Hz, 6H). ¹³C NMR (101 MHz, CDCl₃) δ 166.89, 163.29, 160.81, 160.69, 148.04, 135.17, 132.73, 132.64, 128.95, 128.91, 128.58, 127.46, 127.43, 127.41, 127.39, 123.30, 120.59, 119.48, 119.35, 119.15, 119.02, 117.73, 117.51, 112.28, 60.92, 53.37, 52.12, 50.08, 39.57, 34.13, 30.03, 14.18. LC/MS (ESI+): 473.05.

Example 15: Methyl 2-(4-fluoro-3-(trifluoromethyl) benzamido)-5,5,7,7-tetramethyl-4,5,6,7-tetrahydrothieno[2,3-c]pyridine-3-carboxylate (GP1-19)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature then 4-fluoro-3-(trifluoromethyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.45 (s, 1H), 8.32 (s, 1H), 8.18 (s, 1H), 7.37 (t, J=8.0 Hz, 1H), 3.93 (s, 3H), 2.71 (s, 2H), 1.53 (s, 6H), 1.27-1.16 (m, 16H). LC/MS (ESI+): 441.07.

Example 16: Methyl 5,5,7,7-tetramethyl-2-(2-(trifluoromethyl)benzamido)-4,5,6,7-tetrahydrothieno[2,3-c]pyridine-3-carboxylate (GP1-22)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature then 2-(trifluoromethyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 11.67 (s, 1H), 7.78 (d, J=7.4 Hz, 1H), 7.66 (dd, J=10.9, 4.5 Hz, 3H), 3.85 (s, 3H), 2.68 (s, 2H), 1.52 (s, 6H), 1.23 (s, 6H). ¹³C NMR (101 MHz, CDCl₃) δ 166.90, 164.03, 147.80, 135.24, 134.04, 132.27, 130.83, 128.57, 128.40, 128.25, 127.92, 126.90, 126.85, 112.18, 52.18, 51.64, 50.17, 39.59, 34.26, 30.90, 30.12, 25.34. LC/MS (ESI+): 441.07.

Example 17: Ethyl 2-(4-bromo-3-(trifluoromethyl) benzamido)-5,5,7,7-tetramethyl-4,5,6,7-tetrahydrothieno[2,3-c]pyridine-3-carboxylate (RS-198)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then 4-bromo-3-(trifluoromethyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.48 (s, 1H), 8.33 (d, J=2.0 Hz, 1H), 7.93 (dd, J=8.3, 2.1 Hz, 1H), 7.85 (d, J=8.3 Hz, 1H), 4.39 (d, J=7.1 Hz, 2H), 2.71 (s, 2H), 1.52 (s, 6H), 1.41 (t, J=7.1 Hz, 3H), 1.23 (s, 6H). ¹³C NMR (101 MHz, CDCl₃) δ 166.92, 161.15, 148.01, 135.69, 131.84, 131.33, 130.87, 128.63, 127.30, 124.82, 124.80, 123.78, 121.06, 112.44, 61.02, 52.34, 50.31, 39.56, 34.17, 30.06, 14.30. LC/MS (ESI+): 534.09.

Example 18: Ethyl 5,5,7,7-tetramethyl-2-(4-morpholinobenzamido)-4,5,6,7-tetrahydrothieno[2,3-c] pyridine-3-carboxylate (RS-7, RS-199)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then the 4-morpholinobenzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.20 (s, 1H), 7.92 (d, J=8.8 Hz, 2H), 6.93 (d, J=8.8 Hz, 2H), 4.38 (q, J=7.1 Hz, 2H), 3.91-3.77 (m, 4H), 3.40-3.22 (m, 4H), 2.70 (s, 2H), 1.52 (s, 6H), 1.41 (t, J=7.1 Hz, 3H), 1.22 (d, J=10.7 Hz, 6H). ¹³C NMR (101 MHz, CDCl₃) δ 166.92, 163.21, 153.96, 149.48, 129.11, 128.16, 122.16, 113.97, 111.07, 66.57, 60.65, 47.64, 39.65, 34.10, 30.09, 25.39, 14.40. LC/MS (ESI+): 472.09.

Example 19: Ethyl 5,5,7,7-tetramethyl-2-(3-(pentafluorosulfanyl)benzamido)-4,5,6,7-tetrahydrothieno [2,3-c]pyridine-3-carboxylate (RS-9, RS-200)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then the 3-(pentafluorosulfanyl)benzoyl chloride (1 equivalent) was added and the reaction was stirred for an additional 1 hour. The solvent was evaporated and the residue was purified by flash-column chromatography on silica gel to provide the desired compound. ¹H NMR (400 MHz, CDCl₃) δ 12.52 (s, 1H), 8.48 (t, J=1.8 Hz, 1H), 8.10 (d, J=7.9 Hz, 1H), 8.01-7.96 (m, 1H), 7.67 (t, J=8.0 Hz, 1H), 4.42 (q, J=7.1 Hz, 2H), 2.78 (s, 2H), 1.59 (s, 6H), 1.43 (d, J=7.1 Hz, 3H), 1.30 (s, 12H). LC/MS (ESI+): 512.05

Example 20: Ethyl 5,5,7,7-tetramethyl-2-(3,4,5-trifluorobenzamido)-4,5,6,7-tetrahydrothieno[2,3-c] pyridine-3-carboxylate (RS-6, RS-202)

2,2,6,6-tetramethylpiperidine (1 equivalent) was stirred with the desired 2-cyanoacetate ester (1 equivalent) and sulfur (1 equivalent) in EtOH for 4 hours at 50° C. The mixture was cooled to room temperature, then 3,4,5-trifluorobenzoyl chloride (1 equivalent) was added and the reaction was stirred for an additional 1 hour. The solvent was evaporated and the residue was purified by flash-column chromatography on silica gel to provide the desired compound. $^1$H NMR (400 MHz, CDCl$_3$) δ 12.44 (s, 2H), 7.67 (dd, J=7.6, 6.4 Hz, 4H), 4.42 (q, J=7.1 Hz, 4H), 2.76 (s, 3H), 1.58 (s, 12H), 1.45 (t, J=7.1 Hz, 6H), 1.29 (s, 12H). LC/MS (ESI+): 440.05

Example 21: Antiparasitic Activity

Figure 14:
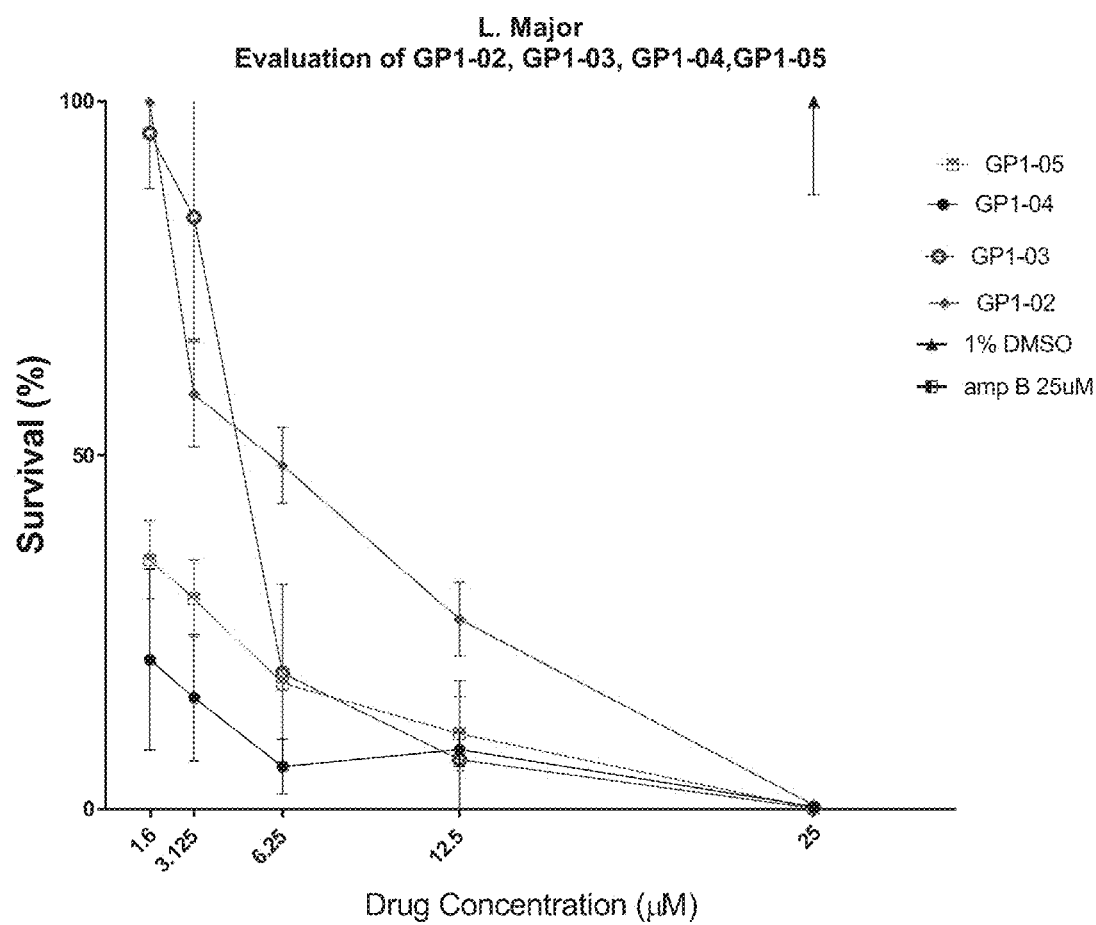
FIGS. 14-15 illustrate antiparasitic activity of compounds GP1-02 to GP1-05.
Figure 15:
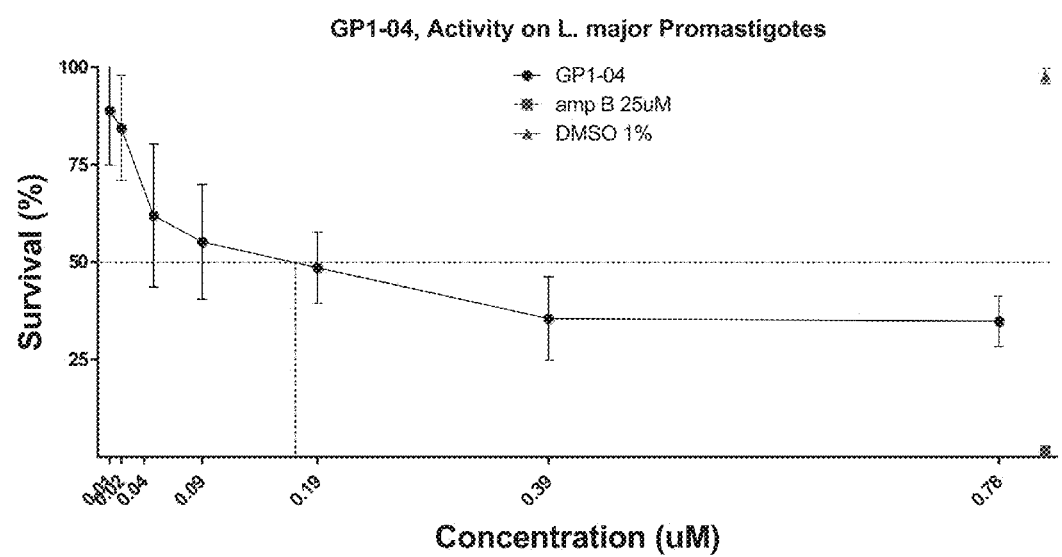

This example illustrates positive effects of treatment with the present compounds. FIG. 14 shows antiparasitic activity of compounds GP1-02-05 in *L. major* Luciferase promastigotes for 72 hr. FIG. 15 shows antiparasitic activity of compound GP1-04 in *L. major* Luciferase promastigotes for 72 hr.

Example 22: Cytotoxicity Evaluation

Figure 16:
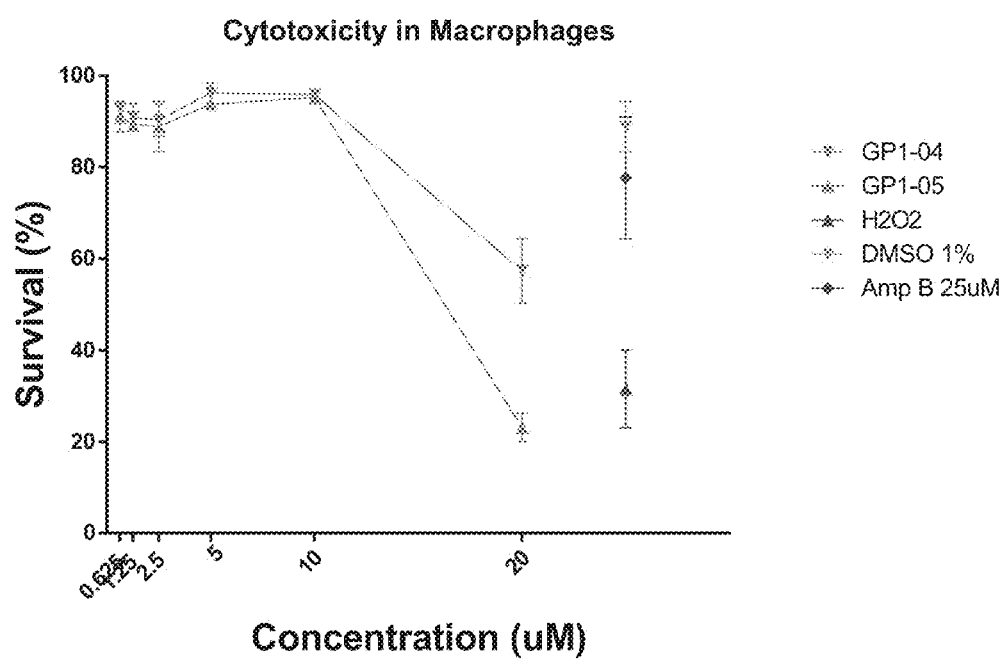
FIG. 16 illustrates a cytotoxicity evaluation of compounds GP1-04 and GP1-05.

This example further illustrates positive effects of treatment with the present compounds. FIG. 16 shows a cytotoxicity evaluation of compounds GP1-04 and GP1-05. The intraperitoneal macrophages (IPΦ) were treated with GP1-04 and GP1-05 for 48 hrs.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure may include descriptions of various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

The invention claimed is:

1. A method of treating a parasitic infection comprising administering to a subject in need of antiparasite treatment an antiparasitic compound having a general formula of Formula I:

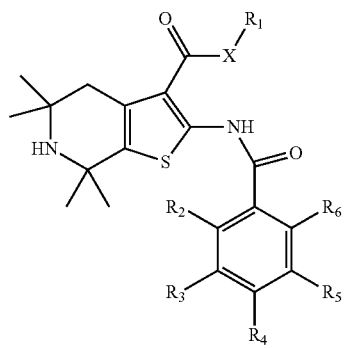

Formula I wherein X is O or N;
R$_1$ is a C2 to C4 alky or C3 to C4 cycloalkyl; and
R$_2$, R$_3$, R$_4$, R$_5$, and R$_6$ are independently selected from hydrogen (H), chlorine (Cl), bromine (Br), fluorine (F), CF$_3$, SF$_5$, substituted or unsubstituted morpholine, substituted or unsubstituted piperazine, boronic acid (B(OH)$_2$), substituted or unsubstituted 1,3,2-dioxaborlane.

2. The method of claim 1, wherein the parasite is *Leishmania major* or *Trypanosoma cruzi*.

3. The method of claim 1, wherein X is O.

4. The method of claim 3, wherein R$_1$ is ethyl, propyl, iso-propyl, cyclopropyl, butyl, isobutyl, sec-butyl or tert-butyl.

5. The method of claim 4, wherein R$_2$, R$_3$, R$_4$, R$_5$, and R$_6$ are independently selected from H, F, CF$_3$, SF$_5$, substituted or unsubstituted morpholine, substituted or unsubstituted piperazine, boronic acid (B(OH)$_2$), substituted or unsubstituted 1,3,2-dioxaborlane.

6. The method of claim 5, wherein R$_2$ and R$_6$ are H, and R$_3$, R$_4$, and R$_5$ are F.

7. The method of claim 5, wherein R$_2$, R$_3$, R$_4$, R$_5$, and R$_6$ are fluorine.

8. The method of claim 5, wherein R$_5$ is CF$_3$, SF$_5$, boronic acid, or 4,4,5,5-tetramethyl-1,3,2-dioxaborlane and R$_2$, R$_3$, R$_4$, and R$_6$ are H.

9. The method of claim 5, wherein R$_2$, R$_3$, R$_5$, and R$_6$ are H, and R$_4$ is morpholine, methyl-piperazine, SF$_5$, boronic acid, or 4,4,5,5-tetramethyl-1,3,2-dioxaborlane.

10. The method of claim 4, wherein R$_2$, R$_3$, R$_4$, R$_5$, and R$_6$ are independently selected from H, Cl, Br, F, and CF$_3$.

11. The method of claim 10, wherein one of R$_2$, R$_3$, R$_4$, R$_5$, and R$_6$ is CF$_3$, another of R$_2$, R$_3$, R$_4$, R$_5$, and R$_6$ is Cl or Br, and the remainder of R$_2$, R$_3$, R$_4$, R$_5$, and R$_6$ are H.

12. The method of claim 1, wherein X is N.

13. The method of claim 12, wherein R$_1$ is ethyl, propyl, iso-propyl, cyclopropyl, butyl, isobutyl, sec-butyl or tert-butyl.

14. The method of claim 13, wherein R$_2$, R$_3$, R$_4$, R$_5$, and R$_6$ are independently selected from H, F, CF$_3$, SF$_5$, substituted or unsubstituted morpholine, substituted or unsubstituted piperazine, boronic acid (B(OH)$_2$), substituted or unsubstituted 1,3,2-dioxaborlane.

15. The method of claim 14, wherein R$_2$ and R$_6$ are H, and R$_3$, R$_4$, and R$_5$ are F.

16. The method of claim 14, wherein $R_2$, $R_3$, $R_4$, $R_5$, and $R_6$ are fluorine.

17. The method of claim 14, wherein $R_5$ is $CF_3$, $SF_5$, boronic acid, or 4,4,5,5-tetramethyl-1,3,2-dioxaborlane and $R_2$, $R_3$, $R_4$, and $R_6$ are H.

18. The method of claim 14, wherein $R_2$, $R_3$, $R_5$, and $R_6$ are H, and $R_4$ is morpholine, methyl-piperazine, $SF_5$, boronic acid, or 4,4,5,5-tetramethyl-1,3,2-dioxaborlane.

19. The method of claim 13, wherein $R_2$, $R_3$, $R_4$, $R_5$, and $R_6$ are independently selected from H, Cl, Br, F, and $CF_3$.

20. The method of claim 19, wherein one of $R_2$, $R_3$, $R_4$, $R_5$, and $R_6$ is $CF_3$, another of $R_2$, $R_3$, $R_4$, $R_5$, and $R_6$ is Cl or Br, and the remainder of $R_2$, $R_3$, $R_4$, $R_5$, and $R_6$ are H.

* * * * *